United States Patent [19]

Leong et al.

[11] Patent Number: 4,806,360

[45] Date of Patent: Feb. 21, 1989

[54] SYNTHETIC MELANIN AGGREGATES

[75] Inventors: Helen Leong, Atherton; Martin Katz, Menlo Park; Anne Delk, Kensington; David Berliner, Atherton; Sergio Nacht, Los Altos, all of Calif.

[73] Assignee: Advanced Polymer Systems, Redwood City, Calif.

[21] Appl. No.: 112,971

[22] Filed: Oct. 23, 1987

[51] Int. Cl.[4] .................... A61K 9/14; A61K 7/42
[52] U.S. Cl. .................... 424/487; 424/59; 424/48; 424/486
[58] Field of Search ............ 424/59, 501, 486, 487

[56] References Cited

U.S. PATENT DOCUMENTS

| | | | |
|---|---|---|---|
| 3,100,180 | 8/1963 | Smith | 424/59 X |
| 3,574,822 | 4/1971 | Shepherd et al. | 424/59 X |
| 3,698,852 | 10/1972 | Pantzer et al. | 8/10.2 |
| 3,821,363 | 6/1974 | Black et al. | 424/59 |
| 3,966,902 | 6/1976 | Chromecek | 424/501 X |
| 4,344,930 | 8/1982 | MacRae et al. | 424/59 X |
| 4,390,341 | 6/1983 | Jacobs | 424/59 X |
| 4,419,343 | 12/1983 | Pauly | 424/59 |
| 4,515,773 | 5/1985 | Herlihy | 424/63 |
| 4,690,825 | 9/1987 | Won | 424/501 |
| 4,741,872 | 5/1988 | De Luca et al. | 424/501 |

Primary Examiner—Thurman K. Page
Attorney, Agent, or Firm—Townsend & Townsend

[57] ABSTRACT

Melanin compositions include a melanin pigment incorporated within an internal pore network defined by a polymeric particle matrix. The melanin compositions may be produced by in situ oxidation of melanin precursors within the pore network, or by absorption of a melanin pigment dispersed in a suitable vehicle or carrier. The melanin compositions are found to display enhanced absorbance of ultraviolet radiation when compared to melanin pigments which are not incorporated in such a polymeric particle matrix.

29 Claims, No Drawings

SYNTHETIC MELANIN AGGREGATES

BACKGROUND OF THE INVENTION

1. Field of the Invention

The present invention relates generally to compositions capable of absorbing ultraviolet radiation, their preparation, and their use as sunscreens. More particularly, the invention relates to synthetic melanin aggregates in the form of a melanin pigment incorporated in a polymer particle matrix.

With growing concern over the deleterious effects of sunlight on human skin, a number of ultraviolet absorbent substances have been identified and developed for use in topical sunscreen compositions. In general, the substances function by absorbing radiation in the ultraviolet radiation region and reemitting the absorbed energy in other, less harmful radiation spectrums.

Although generally effective, most of the sunscreen substances which are presently in widespread use suffer from a number of drawbacks. In particular, most of the sunscreen substances are very oily and are difficult to formulate into suitable products. Such sunscreen substances may also be incompatible with other ingredients in a cosmetic preparation where it would be desirable to incorporate sunscreen protection. Additionally, many sunscreen compositions are characterized by strong odor, usually requiring the addition of a fragrance in order to formulate a commercially acceptable product. Furthermore, the sunscreens are easily lost from the skin either by rubbing or by intradermal penetration. Finally, many of the widely used sunscreen substances can be toxic at high concentrations when absorbed through the skin.

For these reasons, it would be desirable to utilize alternate ultraviolet absorbent substances as the active ingredient in a wide variety of sunscreen and cosmetic formulations. In particular, it would be desirable to identify and provide ultraviolet absorbent substances which are non-penetrating and will not be rapidly lost from the skin. It would be further desirable if such sunscreen substances were non-toxic, even if applied to the skin over open wounds. Such sunscreens should be relatively non-odoriferous, and compatible with a wide variety of sunscreen and cosmetic preparations.

Melanins are a major class of broad-spectrum ultraviolet-absorbing organic polymers found naturally in the human epidermis. They are formed in the epidermis by the enzymatic conversion of L-tyrosine into L-3,4-dihydroxyphenylalanine, commonly referred to as L-dopa. The L-dopa is further converted to a melanin by a biologic pathway which is described in the literature. The primary class of melanins produced in the human epidermis is eumelanins, characterized by a black-brown color and composed primarily of tyrosine-derived units. Pheomelanins constitute a second class of melanins, characterized by a reddish-brown color and composed of cysteine-derived units in addition to tyrosine-derived units.

The use of melanins as the ultraviolet-absorbent substance in sunscreen compositions would have a number of the desirable properties set forth above. They are natural substances and substantially non-toxic even when applied at very high concentrations on the skin. They are free from objectionable odor and appear to be compatible with a wide variety of formulations, including both primary sunscreen formulations and cosmetic formulations. Finally, melanins are not volatile and will not be lost from the skin through evaporation or penetration.

Unfortunately, melanins incorporated in conventional carriers and vehicles, such as lotions, creams, ointments, powders, and the like, have not been found to provide effective protection against exposure to ultraviolet radiation when incorporated in primary sunscreen products or cosmetic formulations.

For that reason, it would be desirable to provide a suitable carrier or vehicle for incorporation of melanin pigments which, when applied topically to the skin, will afford a high level of protection against ultraviolet radiation. It would be particularly desirable if such compositions retained the other advantages which would be expected of melanins, i.e., non-toxicity, compatibility with a wide variety of formulations, freedom from odor, and the like.

2. Description of the Background Art

U.S. Pat. No. 3,698,852, describes a hair dye preparation prepared by the reaction, under alkaline conditions, of at least one dihydroxyphenylalanine or dihydroxyphenylglycine with a phenylamine. U.S. Pat. No. 4,515,773 describes an artificial tanning composition including a suitable dye precursor, such as tyrosine, L-dopa, or the like, in combination with tyrosinase. The tyrosinase catalyzes the conversion of the precursor into melanin-like dyes on the human skin to impart a tan-like appearance.

SUMMARY OF THE INVENTION

According to the present invention, novel melanin compositions comprise melanin pigments entrapped within a pore network defined by a polymeric particle matrix. Surprisingly, incorporation of the melanin pigments within the polymeric particle matrix appears to enhance the ability of the melanins to absorb ultraviolet radiation so that such compositions afford adequate protection from the sun when topically applied to the skin. Such compositions are also non-toxic, compatible with a wide variety of formulations, and substantially free from odor.

The polymeric particle matrix comprises a plurality of polymeric particles, each defining a network of internal pores. The polymeric particles are usually substantially non-collapsible beads having a cross-linking density of at least about 10%, more usually in the range from about 10% to 80%. The average bead diameter will range from about 5 $\mu$m to 100 $\mu$m, usually in the range from about 10 $\mu$m to 40 $\mu$m.

Conveniently, polymeric beads useful in the present invention may be formed by suspension polymerization of suitable monomers in an immiscible phase including a porogen. Generally, the monomers and the porogen are first mixed together, and the resulting mixture then suspended in the immiscible phase, usually an aqueous phase. The immiscible phase is then agitated to form droplets of the monomer mixture, and polymerization of the monomer mixture is initiated to form the desired beads. Once the beads are formed, melanin pigments may be introduced either by in situ oxidation of suitable melanin precursor materials, or by absorption of a dispersion of finely-divided melanin pigments in a suitable vehicle or carrier. The resulting melanin beads are a dry powder which may be used alone, or further incorporated into a primary sunscreen product or cosmetic formulation.

DESCRIPTION OF THE SPECIFIC EMBODIMENTS

The compositions of the present invention are aggregates of melanin pigment contained in a polymeric particle matrix. More specifically, the melanin pigment is entrapped within an internal pore network defined within each of the polymeric particles. The pigments are not normally released from the particles in normal use, i.e., when applied to the skin, and instead it is the aggregate of the pigment in the particle which acts to absorb ultraviolet radiation in accordance with the present invention. Suitable polymeric prticles will not readily undergo unwanted reactions, will be stable over a wide pH range, and will resist moderate oxidation and reduction. The particles should be stable at higher temperatures, resist attack by moisture, and have a relatively long shelf life.

The preferred polymer particle matrix of the present invention comprises rigid polymeric beads having a substantially non-collapsible pore structure. That is, the beads will substantially retain their internal pore structure even after the porogen (used in formation of the bead as described hereinafter) has been extracted and the pores are empty. Such beads are mechanically stable compared with non-rigid materials, allowing manufacturing, processing, and handling of the beads under relatively rigorous conditions which might result in the rupture or damage of less stable materials. More importantly, the non-collapsible pores facilitate introduction of the melanin precursor solution or melanin pigment dispersion, as described in more detail hereinafter.

The rigid polymeric beads of the present invention are formed by polymerization and cross-linking of one or more preselected monomers to form a molecular structure having a substantially non-collapsible network of pores resulting from the presence of the porogen during polymerization. At least one monomer will be polyethylenically unsaturated, and usually the polymer will include a monoethylenically unsaturated co-monomer. The degree of cross-linking may then be controlled by adjusting the ratio of monoethylenically unsaturated monomer to polyethylenically unsaturated monomer, as discussed in more detail hereinbelow. The melanin pigment is entrapped within the network of pores, the resulting melanin aggregates function as an ultraviolet protective composition for topical application, as described in more detail hereinbelow.

The rigid polymer beads of the present invention will have greater than 10% cross-linking, usually having in the range from about 20% to 80% cross-linking, more usually having in the range from about 25% to 60% cross-linking, and typically being in the range from about 45% to 55% cross-linking. The calculated or theoretical percentage of cross-linking is defined as the weight of polyethylenically unsaturated monomer (or monomers) divided by the total weight of monomer, including both polyethylenically unsaturated and monoethylenically unsaturated monomers.

The beads of the polymer are conveniently formed by suspension polymerization in a liquid-liquid system. In general, a solution containing monomers, a polymerization catalyst (if used), and an inert but fully miscible liquid porogen is formed which is immiscible with water. The solution is then suspended in an aqueous solution, which generally contains additives such as surfactants and dispersants to promote the suspension. Once the suspension is established with discrete droplets of the desired size, polymerization is effected (typically by activating the reactants by either increased temperature or irradiation). Once polymerization is complete, the resulting rigid beads are recovered from the suspension. The beads at this point are solid porous structures, the polymer having formed around the inert, water-immiscible liquid, thereby forming the pore network. The liquid porogen has accordingly served as a "pore-forming agent" and occupies the pores of the formed beads.

Materials suitable as porogens will be liquid substances which meet the following criteria:

1. They are either fully miscible with the monomer mixture or capable of being made fully miscible by the addition of a minor amount of non-water-miscible solvent;

2. They are immiscible with water, or at most only slightly soluble;

3. They are inert with respect to the monomers, and stable when in contact with any polymerization catalyst used and when subjected to any conditions needed to induce polymerization (such as temperature and radiation); and 4. They are readily extracted from the pore network of the beads once polymerization is complete.

Suitable porogens include a wide range of substances, notably inert, non-polar organic solvents. Some of the most convenient examples are alkanes, cycloalkanes, and aromatics. Specific examples of such solvents are alkanes of from 5 to 12 carbon atoms, straight or branched chain cycloalkanes of from 5 to 8 carbon atoms, benzene, and alkyl-substituted benzenes, such as toluene and the xylenes. Extraction of the porogen may be effected by solvent extraction, evaporation, or similar conventional operations. The porogen extraction step accomplishes the removal of unwanted species from the polymerized structures prior to impregnation with the desired active substance. Such unwanted species include unreacted monomers, residual catalysts, and surface active agents and/or dispersants remaining on the bead surfaces.

Extraction of the porogen may be effected in a variety of ways, depending on the chemical nature of the porogen and its behavior in combination with that of the other species present. For example, the beads may be recovered from the suspension by filtration, preferably using vacuum apparatus (such as a Beuchner funnel). The beads are then washed with an appropriate solvent to remove organic species not bound to the polymer, inoluding surfactants having deposited on the bead surfaces from the aqueous phase, unreacted monomers and residual catalysts, and the porogen itself. An example of such a solvent is isopropanol, either alone or in aqueous solution. Once washing is complete, the solvent itself is removed by drying, preferably in a vacuum.

In certain cases, an alternative method of extraction may be used—i.e., where the porogen, unreacted monomer and water will form an azeotrope. In these cases, steam distillation is an effective way of extracting porogen from the beads. This again may be followed by drying under vacuum.

Once the beads are rendered dry and free of the porogen and any unwanted organic materials, melanin pigment is introduced to the internal pore networks of the individual beads by either an in situ oxidation procedure or by absorption of a melanin dispersion in a suitable solvent. These methods of introducing the melanin pigment will be described in more detail hereinbelow.

The polymerization process used in preparing the beads of the polymer delivery system can be modified to control both the porosity and the particle diameter of the beads. Particle diameter is controlled primarily by the degree of agitation, with more rigorous agitation causing smaller droplets and hence smaller polymerized beads. The pore diameter and pore volume, in contrast, are controlled primarily by the cross-linking density. Porosity is increased by increasing the amount of cross-linking monomer used, or by increasing the porogen concentration in the monomer mixture, or both. An increase in porosity increases the surface area of the bead and hence the weight percent of the melanin pigment which may be held within the bead. Bead diameter is also affected by the concentration of dispersing agent in the immiscible phase.

The bead diameter in the polymer delivery system should be in the range from about 5 to 100 microns. Beads having an average diameter in the range from about 5 microns to no more than about 70 microns are preferred, with a bead diameter in the range from about 10 microns to about 40 microns being particularly preferred. Beads with a diameter from 10 to 40 microns have been found to be aesthetically pleasing when topically applied to the skin.

The pore dimensions within the beads may vary widely, with optimum dimensions depending on the chemical characteristics of the polymers used as well as the diffusive characteristics of the active substance. Different systems will thus call for different optimum ranges of pore volume distribution to obtain the most desirable properties for the overall formulation. In general, however, best results are obtained with total pore volumes ranging from about 0.1 to about 2.0 cc/g, preferably from about 0.3 to about 1.0 cc/g; pore surface areas ranging from about 1 to about 500 $m^2/g$, preferably from about 20 to about 200 $m^2/g$; and average pore diameters ranging from about 0.001 to about 3.0 microns, preferably from about 0.003 to about 1.0 micron. Following conventional methods of measuring and expressing pore sizes, the pore diameters are measured by techniques such as nitrogen or mercury porosimetry and are based on the model of a pore of cylindrical shape.

In order to form the cross-linked polymer beads of the present invention, it is necessary to polymerize either polyethylenically unsaturated monomers, i.e., those having at least two sites of unsaturation, or to polymerize monoethylenically unsaturated monomers in the presence of one or more polyethylenically unsaturated monomers. In the latter case, the percentage of cross-linking may be controlled by balancing the relative amounts of monoethylenically unsaturated monomer and polyethylenically unsaturated monomer.

Monoethylenically unsaturated monomers suitable for preparing polymer beads for the polymer delivery system include ethylene, propylene, isobutylene, diisobutylene, styrene, ethylvinylbenzene, vinyltoluene, and dicyclopentadiene; esters of acrylic and methacrylic acid, including the methyl, ethyl, propyl, isopropyl, butyl, sec-butyl, tert-butyl, amyl, hexyl, octyl, ethylhexyl, decyl, dodecyl, cyclohexyl, isobornyl, phenyl, benzyl, alkylphenyl, ethoxymethyl, ethoxyethyl, ethoxypropyl, propoxymethyl, propoxyethyl, propoxypropyl, ethoxyphenyl, ethoxybenzyl, and ethoxycyclohexyl esters; vinyl esters, including vinyl acetate, vinyl propionate, vinyl butyrate and vinyl laurate; vinyl ketones, including vinyl methyl ketone, vinyl ethyl detone, vinyl isopropyl ketone, and methyl isopropenyl ketone; vinyl ethers, including vinyl methyl ether, vinyl ethyl ether, vinyl propyl ether, and vinyl isobutyl ether; and the like.

Polyethylenically unsaturated monomers which ordinarily act as though they have only one unsaturated group, such as isoprene, butadiene and chloroprene, may be used as part of the monoethylenically unsaturated monomer content.

Polyethylenically unsaturated cross-linking monomers suitable for preparing such polymer beads include diallyl phthalate, ethylene glycol diacrylate, ethylene glycol dimethacrylate, trimethylolpropanetrimethacrylate, divinylsulfone; polyvinyl and polyallyl ethers of ethylene glycol, of glycerol, of pentaerythritol, of diethyleneglycol, of monothio- and dithioderivatives of glycols, and of resorcinol; divinylketone, divinylsulfide, allyl acrylate, diallyl maleate, diallyl fumarate, diallyl succinate, diallyl carbonate, diallyl malonate, diallyl oxalate, diallyl adipate, diallyl sebacate, divinyl sebacate, diallyl tartrate, diallyl silicate, triallyl tricarballylate, triallyl aconitate, triallyl citrate, triallyl phosphate, divinyl naphthalene, divinylbenzene, trivinylbenzene; alkyldivinylbenzenes having from 1 to 4 alkyl groups of 1 to 2 carbon atoms substituted on the benzene nucleus; alkyltrivinylbenzenes having 1 to 3 alkyl groups of 1 to 2 carbon atoms substituted on the benzene nucleus; trivinylnaphthalenes, and polyvinylanthracenes.

The particularly preferred polymer delivery system of the present invention is formed by the copolymerization of methylmethacrylate and ethylene glycol dimethylmethacrylate. Usually, the methylmethacrylate will be present at from about 10 to 80 percent of the monomer mixture, more usually at about 20 to 60 percent of the monomer mixture, typically being in the range from about 45 to 55 percent of the monomer mixture, with the ethylene glycol dimethylmethacrylate forming the remainder of the mixture.

Melanins suitable for incorporation in the polymeric particle matrix of the present invention include any of the wide variety of black-brown and reddish-brown polymers of indole 5,6-quinone and 5,6-dihydroxyindole 2-carboxylic acid that occur naturally in the skin, hair, retina, and elsewhere in humans, as well as in a variety of other organisms. In particular, eumelanins, which are black-brown polymers composed primarily of tyrosine-derived units, and pheomelanins, which are composed of cysteine-derived units in addition to tyrosine-derived units, will be employed.

The melanins may be introduced to the polymeric particle matrix either by in situ oxidation of suitable melanin precursor materials, and/or by absorption of a dispersion of melanin pigment in a suitable carrier or vehicle.

Suitable melanin precursors include but are not limited to tyrosine, 3,4-dihydroxy phenylalanine (dopa), D-dopa, catechol, 5-hydroxyindole, tyramine, dopamine, m-aminophenol, o-aminophenol, p-aminophenol, 4-aminocatechol, 2-hydroxyl-1,4-naphthaquinone (henna), 4-methyl catechol, 3,4-dihydroxybenzylamine, 3,4-dihydroxybenzoic acid, 1,2-dihydroxynaphthalene, gallic acid, resorcinol, 2-chloroaniline, p-chloroanisole, 2-amino-p-cresol, 4,5-dihydroxynaphthalene 2,7-disulfonic acid, o-cresol, m-cresol, p-cresol, and other related substances which are capable of being oxidized to tan, brown, or black compounds capable of absorbing ultraviolet radiation when incorporated in the polymeric particle matrix of the present invention. Combinations of precursors can also be used.

The melanin precursor is dissolved in an aqueous solution, typically at an elevated temperature to achieve complete solution. A suitable amount of the enzyme tyrosine (EC 1.14.18.1) is added to the solution, either before or after the melanin precursor. The concentration of tyrosinase is not critical, typically being present in the range from about 50 to about 5000 U/ml. The solution is buffered with an acetate, phosphate, or other suitable buffer, to a pH in the range from about 3 to 10, usually in the range from about 5 to 8, more usually being about 7.

The solution of melanin precursor and tyrosinase is then combined with a suitable volume of dry polymeric matrix particles usually at a weight ratio of from about 3:1 to 1:3 particles:precursors solution, more usually in the range from about 2:1 to 1:2 particles:precursors. The mixture of the beads and precursor solution is agitated so that the precursor solution is absorbed within the internal pores of the polymer particles. The mixture is then held, typically at about room temperature, for a sufficient period of time for oxidation and polymerization of the precursors into the desired melanins to occur. Using such in situ melanin formation, melanin concentrations in the range from about 0.2 to 3.5 weight percent in the final product may be achieved in a single oxidation step. Melanin concentrations in the range from about 20 to 30 weight percent may be achieved by multiple in situ synthesis steps.

Desirably, the concentration of melanin precursor may be increased by dissolving the precursor in an alkaline aqueous solution, typically in the range from about 8 to 14, usually in the range from about 9 to 13, more usually being in the range from about 11 to 12. The alkaline solution may also be heated to cause complete dissolution of the precursor. A suitable amount of an oxidizing agent, such as ammonium persulfate, ferric chloride, magnesium perchlorate, benzoyl peroxide, and the like, may be added to promote oxidation of certain of the melanin precursors. In this way, melanin concentrations in the range from about 0.5 to 10% may be achieved in a single oxidation step, and melanin concentrations in the range from about 30 to 40% may be achieved in multiple oxidation steps.

Melanin pigment may also be introduced to the polymeric particles of the present invention by absorption of a dispersion of finely divided melanin pigment together with solubilized melanin (as described below) in a suitable carrier vehicle into the particles. Melanins may be obtained commercially, or may be prepared by the enzymatic or chemical oxidation of suitable precursors as described above. Once the melanin pigments are obtained, they will usually exist in the form of a finely-divided powder, typically having a particle size in the range from about 0.01 to 0.1 microns. If the particles are any larger, they should be reduced in size to within the stated range. The larger particles will generally not be dispersed and absorbed into the pores of the polymeric particles.

The melanin pigment powders are then dispersed in a suitable carrier or vehicle, such as water buffer, alkali, or other suitable solvent. The dispersion is then absorbed within the polymeric particles by contact absorption, followed by drying to evaporate the carrier or vehicle. Amounts of melanin in the range from about 3 to 6 weight percent of the final composition may be introduced in a single absorption step. The weight concentrations of the melanin pigment as high as 30 to 40 weight percent may be achieved by multiple absorption steps.

The melanin compositions just described are a dry powder having an aesthetically pleasing sensation when applied topically to the skin. The melanin compositions may be used alone and applied to the skin as a powder or may be incorporated in a suitable carrier base as a primary sunscreen product. Alternatively, the melanin compositions may be incorporated in other cosmetic preparations, such as skin, face and body creams, decorative cosmetics such as foundation creams and make-up powders, lipsticks, lip balms, hair grooming preparations, and the like, where they will be generally free from interaction with other active substances in the formulations.

The following examples are offered by way of illustration, not by way of limitation.

EXPERIMENTAL

Materials and Methods

1. Preparation of Copolymer Beads from Styrene and Divinylbenzene

A two-liter four-necked reaction flask equipped with a stirrer driven by a variable speed motor, reflux condenser, thermometer, and nitrogen-inlet tube was set up. A slow flow of nitrogen was maintained through the reaction flask at all times. An aqueous phase made up at 350 parts of deionized water, 1.8 parts of gum arabic, and 1.8 parts sodium lignosulfate (Marasperse N-22, available from Reed Lignin, Inc.) was added to the flask, and an organic solution made up 39.65 parts of styrene, 47.60 parts of commercial divinylbenzene (55.6% divinylbenzene, 42.3% ethylvinylbenzene), 71.35 parts of heptane, and 2.2 parts benzoyl peroxide (70% active ingredient and 30% water) was dispersed in the aqueous phase with rapid agitation (stirrer speed approximately 950 rpm) to obtain a plurality of droplets having an average droplet diameter of below about 60 microns as determined by visual observation of a sample of the droplets with an optical microscope.

The reaction mixture was then heated to about 75° C. and maintained at that temperature for 10 hours to form porous beads of cross-linked styrene/divinylbenzene copolymer having heptane entrapped within the pores. The reaction mixture was then cooled to room temperature and the resulting polymeric beads collected by filtration, washed three times with 1000 parts of deionized water, and three times with 1000 parts of acetone, then dried in a vacuum oven at 80.C for 24 hours.

The calculated or theoretical cross-link density of the purified beads was 30.3%. This density was calculated by multiplying the weight of divinylbenzene (47.6 g) by the purity of the divinylbenzene (0.556) to get the actual weight of pure divinylbenzene which is then divided by the total weight of monomer (87.25 g).

The surface area of a sample of the purified beads was 146.2m2/g as measured by B.E.T. nitrogen multipoint analysis and the pore volume was 0.99 ml/g as measured by Mercury porosimetry.

2. Preparation of Copolymer Beads from Methylmethacrylate and Ethyleneglycol Dimethacrylate A two-liter-necked reaction flask equipped as described above was evacuated and purged with nitrogen. An aqueous phase made up of 450 parts of deionized water, 4 parts of gum arabic, and 4 parts of sodium lignosulfate was added to the flask, and an organic solution made up 52 parts of methylmethacrylate, 78 parts ethyleneglycol dimethacrylate, 1.5 parts of benzoyl peroxide (70% in water), and 150 parts of toluene was dispersed in the aqueous phase with rapid stirring (stirrer speed approximately 900 rpm) to obtain a plurality of droplets having an average droplet size of below about 60 microns, as determined by visual observation of a sample of the droplets being stabilized by the dispersants.

The reaction mixture was heated to 65° C for 1 hour, then 75.C and allowed to remain at this temperature for approximately 7 hours while maintaining a nitrogen flow of 2 ml/minute to form porous beads of cross-linked methacrylate/ethyleneglycoldimethacrylate copolymer having toluene entrapped within the pores. The reaction mixture was then cooled and the beads collected by filtration, washed three times with 1000 parts of deionized water, and three times with 1000 parts of acetone, then dried in a vacuum oven at 80° C. for about 24 hours.

The calculation of theoretical cross-link density of the purified beads was 60%, calculated by dividing the weight of ethyleneglycoldimethacrylate (78 g) by the weight of monomer (130 g).

The surface area of a sample was 180.59 m$^2$/g and the pore volume was 0.684 ml/g, determined as described above.

3. In situ Synthesis of Melanin from L-dopa via Tyrosinase Catalysis

Twenty-five milligrams (25 mg) of L-dihydroxyphenylalanine (L-dopa) was added to ten milliliters (10 ml) of fifty millimolar (50 mM) monobasic potassium phosphate ($KH_2PO_4$), which had been previously adjusted to pH 7.0 with sodium hydroxide (NaOH). The mixture was warmed to about 50° C. and agitated to make a solution. One milligram (1 mg) of tyrosinase was dissolved in the above solution.

Six grams (6 g) of dry methacrylate copolymer beads were added to four milliliters (4 ml) of the Dopa-tyrosinase solution. Similarly, six grams (6 g) of dry styrene copolymer beads were added to four milliliters (4 ml) of the Dopa-tyrosinase solution. The solutions were each distributed throughout and absorbed into the dry beads by manual mixing with the aid of a spatula or other stirring device.

The mixtures were held at room temperature in a moist atmosphere for eighteen hours, then dried at 80° C. for six hours.

4. In situ Synthesis of Melanin from L-dopa and Cysteine via Tyrosinase Catalysis 50 mg of L-dopa was dissolved in 25 ml of potassium phosphate, solution which was prepared as described above. 30 mg of L-cysteine was dissolved in 25 ml of potassium phosphate solution prepared as described above. I mg of tyrosinase was dissolved in 10 ml of potassium phosphate solution prepared as described above.

3.75 ml of the dopa solution was mixed with 0.25 ml of the cysteine solution. 0.5 ml of tyrosinase solution was added to the mixture of dopa and cysteine.

Six grams of dry beads of either methacrylate or styrene composition was added to 4 ml of the Dopa-cysteine-tyrosinase mixture and a homogeneous mixture prepared as described above. Alternatively, the dopa solution and the cysteine solution were mixed at other ratios, for example 3.40 ml of dopa solution with 0.60 ml cysteine solution. 0.5 ml of tyrosinase solution was added to the Dopa-cysteine mixture.

Six grams of dry microsponge of either methacrylate or styrene composition was added to 4 ml of the Dopa-cysteine-tyrosinase mixture and a homogeneous mixture prepared as described above.

The moist mixture was held at room temperature in a moist atmosphere for 18 hours, then dried as described above.

5. In situ Synthesis of Melanin from L-dopa via Autooxidation 50 mg of L-dopa was dissolved in 5 ml of potassium phosphate solution, prepared as described above, to which had been added 0.1 ml of concentrated ammonium hydroxide. 500 mg of dry methacrylate beads was added to 0.33 ml or 0.67 ml of the dopa solution. A homogeneous mixture was prepared, held in a moist atmosphere, and finally dried as described above. Melanin beads having a melanin content of 0.7 weight percent and 1.4 weight percent were obtained.

6. Preparation of Melanin Beads via Absorption of Melanin formed by Oxidation of Tyrosine 50 or 250 mg of commercially available melanin (prepared by chemical oxidation of tyrosine with persulfate and autopolymerization of the oxidation products) was mixed with 5 ml of 1 N ammonium hydroxide ($NH_4OH$) Six g of dry methacrylate beads were mixed with 4 ml of the melanin mixture and dried for 6 hr as described above. Melanin beads having a melanin content of 0.6 weight percent and 3.0 weight percent were obtained.

7. Preparation of Melanin Beads via Absorption and in situ Synthesis

One gram of melanin, prepared by oxidation of tyrosine as described above, was mixed with six ml of ammonium hydroxide ($NH_4OH$) solution, also as described above. 300 mg of L-dopa was dissolved in the melanin solution. 5.5 g of dry methacrylate beads were added to the above mixture. A homogeneous mixture was prepared and held in a moist atmosphere. The melanin beads were recovered and separated from excess melanin mixture by filtration using a Beuchner funnel, and the separated beads washed with 50 mM ammonium acetate, pH 4. The beads were then dried as described above.

8. Preparation of Bleached Melanin Beads 20 mg of commercially available melanin was mixed with 0.4 ml of IN ammonium hydroxide. 600 mg of dry methacrylate beads were mixed with the resulting mixture and dried as described above for 18 hours. Melanin beads having a melanin content of 3.3 weight percent were obtained. 100 mg of the dried melanin beads were mixed with 0.4 ml of 3% $H_2O_2$ and allowed to stand for 24 hr. The dry beads so treated were bleached from a dark brown/black color to a much lighter tan color.

Results

Melanin beads prepared as described in sections 5 and 6 above were suspended in a mixture of glycerol and isopropanol (1:2, by weight) at 2.5 mg/ml. The samples were placed in a cuvette with a 1 cm light path length, and optical densities were measured as absorbance in a Beckman DU-50 Spectrophotometer. The melanin beads were found to display enhanced absorbance in comparison to untreated bead samples, and absorption increased with increasing melanin concentration. The results are set forth in Table 1.

TABLE 1.

Comparison of the Optical Densities of Melanin Beads and Untreated Beads

| Preparation | Wavelength | | | |
|---|---|---|---|---|
| | 250 nm | 300 nm | 350 nm | 400 nm |
| Melanin Beads: | | | | |
| 1. Melanin Absorption (3.0%) | ND | ND | 1.42 | 1.22 |
| 2. Melanin Absorption (0.6%) | 1.20 | 0.78 | 0.64 | 0.54 |
| 3. In Situ Synthesis (<1.4%) | ND | 1.30 | 0.97 | 0.82 |
| 4. In Situ Synthesis (<0.7%) | ND | 1.14 | 0.85 | 0.70 |
| Untreated Beads | 0.82 | 0.52 | 0.42 | 0.36 |

ND: Not determined

Melanin beads prepared as described in section 7 above, untreated beads, or charcoal powder, were suspended in a tranparent gelatinous material. Samples having a thickness of about 0.07 to 0.09 mm were placed in the light path of a Beckman DU-50 Spectrophotometer and the average percent of light transmission between 250-290, 990-320, and 320-400 nm determined. Blocking ability is expressed as a percentage obtained by substracting the transmission percent from 100%. The results are set forth in Table 2.

TABLE 2

Comparison of Irradiation Blocking Abilities of Melanin Beads, Untreated Beads and Charcoal

| Sample | Wavelength (nm) | | |
|---|---|---|---|
| | 250-290 | 290-320 | 320-400 |
| 5.3% Melanin Beads, 0.3% melanin final | 84% | 80% | 75% |
| 5.0% Untreated Beads | 48% | 45% | 44% |
| 4.8% Charcoal | 51% | 53% | 54% |

Bleached and unbleached melanin beads were prepared as described in section 8 above. The melanin beads and untreated beads were mixed with a transparent gelatinous material at 4.8% by weight. Samples of 0.07 to 0.09 mm in thickness were placed in the light path of a Beckman DU-50 Spectrophotometer. The average percent of light transmission was measured, as set forth in Table 3.

TABLE 3

Comparison of the Percent Transmission of Melanin Beads, Bleached Melanin Beads and Untreated Beads at Different Wavelengths

| Preparation | Wavelength (nm) | | |
|---|---|---|---|
| | 250-290 | 290-320 | 320-400 |
| Melanin Beads | 6% | 10% | 20% |
| Bleached Melanin Beads | 20% | 27% | 35% |
| Untreated Beads | 42% | 45% | 48% |

Although the foregoing invention has been described in some detail by way of illustration and example for purposes of clarity of understanding, it will be obvious that certain changes and modifications may be practiced within the scope of the appended claims.

What is claimed is:

1. A composition comprising substantially non-collapsible particles each defining a network of internal pores and having melanin pigment entrapped within said network of pores, wherein said particles are polymers having a cross-linking density of at least about 10% and said melanin pigment has been introduced to said pores by absorption of melanin pigment or by in situ conversion of a melanin precursor within said pores.

2. A composition as in claim 1, wherein said polymeric particles are substantially non-collapsible beads.

3. A composition as in claim 1, wherein the polymeric beads are a styrene-divinylbenzene copolymer.

4. A composition as in claim 1, wherein said cross-linking density is in the range from about 20% to 80%.

5. A composition as in claim 2, wherein said beads have an average diameter in the range from about 5 $\mu$m to 100 $\mu$m.

6. A composition as in claim 5, wherein said average diameter is in the range from about 10 $\mu$m to 40 $\mu$m.

7. A composition as in claim 1, wherein the polymeric beads are a methyl methacrylate-ethylene glycol dimethacrylate copolymer.

8. A composition as in claim 1, wherein the melanin precursor is selected from the group consisting of L-dopa, tyrosine, tryptophan, and cysteine.

9. A composition as in claim 1, wherein the melanin precursor is L-dopa.

10. A composition as in claim 1, wherein the melanin pigment is introduced into preformed beads by absorption of a dispersion of melanin pigment in a suitable carrier, followed by evaporation of the carrier.

11. A composition as in claim 10, wherein the carrier is selected from the group consisting of water, buffer, and alkaline solution.

12. A method for preparing a melanin particle composition, said method comprising:
    introducing a melanin precursor into a plurality of substantially non-collapsible polymeric particles having a cross-linking density of a least about 10% and each defining a network of internal pores; and
    oxidizing the melanin precursor to melanin pigment within said pores.

13. A method as in claim 12, wherein the melanin precursor is selected from the group consisting of L-dopa, tyrosine, tryptophan, and cysteine.

14. A method as in claim 12, wherein the oxidation is promoted by an oxidation catalyst.

15. A method as in claim 14, wherein the oxidation catalyst is an enzyme.

16. A method as in claim 15, wherein the enzyme is tyrosinase.

17. A method for preparing a melanin particle composition, said method comprising:
    introducing a dispersion of melanin pigment in a suitable carrier into a plurality of substantially non-collapsible polymeric particles having a cross-linking density of at least about 10% and each defining a network of internal pores; and
    evaporating the carrier from the pores of the particles.

18. A method as in claim 17, wherein the carrier is selected from the group consisting of water, buffer, and alkaline solution.

19. A method as in claim 17, wherein the melanin is in the form of a finely divided powder.

20. A method for protecting skin from exposure to ultraviolet radiation, said method comprising:
    applying to the skin a composition comprising substantially non-collapsible polymeric particles having a cross-linking density of at least about 10% and each defining a network of internal pores and having melanin pigment entrapped within said network of pores, wherein said melanin pigment has been introduced to said pores by absorption of melanin pigment or by in situ conversion of a melanin precursor within said pores.

21. A method as in claim 20, wherein said cross-linking density is in the range from about 20% to 80%.

22. A method as in claim 20, wherein said beads have an average diameter in the range from about 5 μm to 100 μm.

23. A method as in claim 22, wherein said average diameter is in the range from about 10 μm to 40 μm.

24. A method as in claim 20, wherein the melanin precursor is selected from the group consisting of L-dopa, tyrosine, tryptophan, and cysteine.

25. A method as in claim 20, wherein the melanin precursor is L-dopa.

26. A method as in claim 20, wherein the melanin pigment is introduced into preformed beads by absorption of a dispersion of melanin pigment in a suitable carrier, followed by evaporation of the carrier.

27. A method as in claim 26, wherein the carrier is selected from the group consisting of water, buffer, and alkaline solution.

28. A method as in claim 20, wherein the polymeric beads are a styrene-divinylbenzene copolymer.

29. A method as in claim 20, wherein the polymeric beads are a methyl methacrylate-ethylene glycol dimethacrylate copolymer.

* * * * *